United States Patent [19]
Boyan et al.

[11] Patent Number: 5,977,204
[45] Date of Patent: *Nov. 2, 1999

[54] BIODEGRADABLE IMPLANT MATERIAL COMPRISING BIOACTIVE CERAMIC

[75] Inventors: Barbara D. Boyan; Gabriele Niederauer; Kristine Kieswetter; Neil C. Leatherbury, all of San Antonio, Tex.; David C. Greenspan, Gainesville, Fla.

[73] Assignees: OsteoBiologics, Inc., San Antonio, Tex.; USBiomaterials Corporation, Alachua, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/838,921

[22] Filed: Apr. 11, 1997

[51] Int. Cl.$^6$ .................................. C08K 3/32; A61F 2/00
[52] U.S. Cl. ......................... 523/113; 523/115; 524/414; 524/417; 524/494; 525/415; 525/450; 623/16; 623/16 C
[58] Field of Search .................................. 523/113, 115; 524/417, 414, 494; 525/415, 450; 623/16, 16 C

[56] References Cited

U.S. PATENT DOCUMENTS

| | | | |
|---|---|---|---|
| 4,103,002 | 7/1978 | Hench et al. | 501/2 |
| 4,171,544 | 10/1979 | Hench et al. | 3/1.9 |
| 4,189,325 | 2/1980 | Barrett et al. | 106/35 |
| 4,192,021 | 3/1980 | Deibig et al. | 3/1.9 |
| 4,234,972 | 11/1980 | Hench et al. | 3/1.9 |
| 4,478,904 | 10/1984 | Ducheyne et al. | 428/288 |
| 4,619,655 | 10/1986 | Hanker et al. | 623/16 |
| 4,676,796 | 6/1987 | Merwin et al. | 623/10 |
| 4,775,646 | 10/1988 | Hench et al. | 501/2 |
| 4,851,046 | 7/1989 | Low et al. | 106/35 |
| 5,017,627 | 5/1991 | Bonfield et al. | 523/115 |
| 5,074,916 | 12/1991 | Hench et al. | 106/35 |
| 5,204,382 | 4/1993 | Wallace et al. | 523/113 |
| 5,223,029 | 6/1993 | Oonishi et al. | 106/35 |
| 5,486,598 | 1/1996 | West et al. | 530/338 |
| 5,503,164 | 4/1996 | Friedman | 623/16 |
| 5,527,836 | 6/1996 | Yamamuro et al. | 523/115 |
| 5,552,454 | 9/1996 | Kretschmann et al. | 523/113 |
| 5,607,474 | 3/1997 | Athanasiou et al. | 623/11 |
| 5,679,723 | 10/1997 | Cooper et al. | 623/16 |
| 5,697,980 | 12/1997 | Otani et al. | 623/16 |

FOREIGN PATENT DOCUMENTS

| | | |
|---|---|---|
| WO 91/17777 | 11/1991 | WIPO . |
| WO 96/00536 | 1/1996 | WIPO . |
| WO 96/19248 | 6/1996 | WIPO . |

OTHER PUBLICATIONS

Greenspan et al. (1994), "Effect of Surface Area to Volume Ratio on In Vitro Surface Reactions of Bioactive Glass Particulates," *Bioceramics* 7:55–60.

Hench, L.L. (1995) "Bioactive Implants," *Chemistry and Industry*, Jul. 17, n.14, pp. 547–550.

*Primary Examiner*—Andrew E. C. Merriam
*Attorney, Agent, or Firm*—Greenlee, Winner and Sullivan, P.C.

[57] ABSTRACT

Biodegradable polymeric therapeutic implant materials incorporating bioactive ceramics such as Bioglass® ceramic are provided. These implants provide increased mechanical properties and pH control, enabling the use of these materials to design porous and nonporous therapeutic implants used as cell scaffolds for healing of tissue defects or fixation devices, having desired degradation times, mechanical properties, elasticity and biocompatibility.

27 Claims, 5 Drawing Sheets

BIODEGRADABLE IMPLANT MATERIAL COMPRISING BIOACTIVE CERAMIC

BACKGROUND OF THE INVENTION

Bioactive ceramic materials are known to the art, and typically contain less than 60 mole percent $SiO_2$, high sodium and CaO content (20–25% each), and a high molar ratio of calcium to phosphorus (ranging around five). Such materials are called "bioactive" because interfacial bonds form between the material and surrounding tissues. When such glasses are exposed to water or body fluids, several key reactions occur. The first is cation exchange wherein interstitial sodium and calcium ions from the glass are replaced by protons from solution, forming surface silanol groups and nonstoichiometric hydrogen-bonded complexes:

This cation exchange also increases the hydroxyl concentration of the solution, leading to attack of the fully dense silica glass network to produce additional silanol groups and controlled interfacial dissolution:

As the interfacial pH becomes more alkaline and the concentration of hydrolyzed surface silanol groups increases, the conformational dynamics attending high numbers of proximal silanol groups, combined with the absence of interstitial ions, cause these groups to repolymerize into a silica-rich surface layer:

Another consequence of alkaline pH at the glass-solution interface is crystallization into a mixed hydroxyapatite phase of the CaO and $P_2O_5$ that were released into solution during the network dissolution. This takes place on the $SiO_2$ surface. This phase contains apatite crystallites which nucleate and interact with interfacial components such as glycosaminoglycans, collagen and glycoproteins. It is thought that incorporation of organic biological constituents within the growing hydroxyapatite- and $SiO_2$-rich layers triggers close interactions with living tissues characteristic of bioactivity. See Greenspan et al. (1994), Bioceramics 7:55–60.

Use of bioactive ceramics in implant prosthetic devices and coatings for prosthetic devices has been described, e.g. in U.S. Pat. No. 4,775,646 to Hench et al. issued Oct. 4, 1988 for "Fluoride-Containing Bioglass® Compositions" which teaches a glass formulation containing 46.1 mole percent $SiO_2$, 2.6 mole percent $P_2O_5$, 26.9 mole percent CaO and 24.4 mole percent $Na_2O$, or 52.1 mole percent $SiO_2$, 2.6 mole percent $P_2O_5$, 23.8 mole percent CaO and 21.5 mole percent $Na_2O$, and compositions in which 40 to 60 mole percent of the CaO is substituted with $CaF_2$. The patent states that implants made of this material are useful where optimization of durable chemical bonding with living tissue is desirable.

Alkali-free bioactive glass compositions based on $SiO_2$, CaO and $P_2O_5$ are disclosed in U.S. Pat. No. 5,074,916 to Hench et al. issued Dec. 24, 1991 for "Alkali-Free Bioactive Sol-Gel Compositions."

Bioglass® is a registered trademark of the University of Florida licensed to USBiomaterials Corporation. Other issued patents related to this material include U.S. Pat. No. 5,486,598 issued Jan. 23, 1996 to West, et al. for "Silica Mediated Synthesis of Peptides," U.S. Pat. No. 4,851,046 issued Jul. 25, 1989 to Low et al. for "Periodontal Osseous Defect Repair," U.S. Pat. No. 4,676,796 issued Jun. 30, 1987 to Merwin et al. for "Middle Ear Prosthesis," U.S. Pat. No. 4,478,904 issued Oct. 23, 1984 to Ducheyne et al. for "Metal Fiber Reinforced Bioglass® Compositions," U.S. Pat. No. 4,234,972 issued Nov. 25, 1980 to Hench et al. for "Bioglass®-Coated Metal Substrate," and U.S. Pat. No. 4,103,002 issued Jul. 25, 1978 to Hench et al. for "Bioglass® Coated A1203 Ceramics." Pending applications include Patent Cooperation Treaty Publication WO 9117777 published Nov. 28, 1991, Walker, et al., inventors, for "Injectable Bioactive Glass Compositions and Methods for Tissue Reconstruction," claiming a priority date of May 22, 1990 based on a U.S. application.

PerioGlas® is a registered trademark of USBiomaterials Corporation licensed to Block Drug Corporation. It refers to a synthetic bone graft particulate material containing Bioglass® ceramic. Product literature describes this material as bonding to both bone and soft tissue, and indicates it is packed directly into a bone defect. Hench, L. L. (1995) "Bioactive Implants," Chemistry and Industry (July 17, n. 14, pp.547–550), reports that collagen fibrils in the surrounding tissue interact directly with the surface layer which forms on bioactive glass.

PCT Publication WO 96/00536, published Jan. 11, 1996, Ducheyne et al. inventors, discloses a method of forming osseous tissue comprising filling an osseous defect with a bioceramic material.

Composite materials comprising particulate bone replacement material have been described, e.g. in U.S. Pat. No. 4,192,021 issued Mar. 11, 1980 to Deibig et al. for "Bone Replacement or Prosthesis Anchoring Material." This patent teaches bone replacement prosthesis anchoring materials which are mixtures of sintered calcium phosphates and biodegradable organic materials at a ratio of calcium phosphate to organic materials between 10:1 and 1:1.

U.S. Pat. No. 5,017,627, issued May 21, 1991, to Bonfield et al. for "Composite Material for Use in Orthopaedics" discloses an apparently non-biodegradable polyolefin material containing particulate inorganic solid particles for bone replacement materials.

U.S. Pat. No. 5,552,454 issued Sep. 3, 1996 to Kretschmann et al. for "New Materials for Bone Replacement and for Joining Bones or Prostheses" discloses compositions comprising biodegradable waxes or polymeric resins (molecular weight 200 to 10,000) and a body-compatible ceramic material, wherein the polymer is substantially free from free carboxyl groups.

Other bioactive ceramics are disclosed in U.S. Pat. No. 4,189,325 issued Feb. 19, 1980 to Barrett et al. for "Glass-Ceramic Dental Restorations," and U.S. Pat. No. 4,171,544 issued Oct. 23, 1979 to Hench et al. for "Bonding of Bone to Materials Presenting a High Specific Area, Porous, Silica-Rich Surface."

PCT Publication WO 96/19248 published Jun. 27, 1996 for "Method of Controlling pH in the Vicinity of Biodegradable Implants and Method of Increasing Surface Porosity," discloses the use of bioactive ceramics as pH-controlling agents in biodegradable polymeric implants.

Composite materials for bone and tissue-healing use made with biodegradable polymers having molecular weights above about 10,000 do not appear to have been disclosed in the literature, nor have the advantageous properties of these materials been reported.

All publications referred to herein are hereby incorporated by reference in their entirety.

BRIEF SUMMARY OF THE INVENTION

This invention provides both porous and nonporous therapeutic implant materials comprising a biodegradable polymer and a bioactive ceramic. Such implants comprising biodegradable polymer and bioactive ceramic are termed "composite implants" herein. Incorporation of bioactive ceramic into the polymer has a number of advantages.

An important advantage is that the material has better mechanical properties (e.g. Young's modulus is higher) than in polymeric materials without the bioactive ceramic. Porous implant materials of this invention are preferably used as cell scaffolds, for placing in defects of cancellous (spongy, trabecular) bone. The Young's modulus of such bone ranges from approximately 10 MPa to 3000 MPa. The porous implant material preferably has a Young's modulus similar to that of the bone in which it is to be placed. These porous implant materials may also be used for cell scaffolds for placing in other types of bone. They may also be used as bone graft substitutes, bone onlays and for spinal fusion. Porous implant materials of this invention preferably have a Young's modulus measured under physiological conditions (37° C. in an aqueous environment) by the three point bending dynamic mechanical analysis described herein between about 0.1 MPa and about 100 MPa, and preferably between about 0.5 MPa and about 50 MPa, and a porosity greater than about 50%, and preferably between about 65% and about 75%, although higher porosities, e.g., up to about 90%, may also be used.

Porous implant materials of this invention may also be used for repair of soft connective tissues such as tendons, ligaments, and skin. The porous scaffold serves as a substrate for guided tissue regeneration. As the biodegradable polymer degrades, it is replaced by new healthy tissue. The surface of the bioactive ceramic component interacts with extracellular matrix components, particularly collagen type I, enhancing wound healing by providing biological surfaces for mesenchymal cell migration and by causing enhanced apposition of the tissue to the implant. By varying the type of bioactive ceramic used and its concentration within the biodegradable polymer, the biological characteristics of the implant can be tailored. Multiphase implants, e.g. as described in U.S. Pat. No. 5,607,474 issued Mar. 4, 1997 to Athanasiou et al. for "Multi-Phase Bioerodible Implant/Carrier and Method of Manufacturing and Using Same," modified to contain bioactive ceramic, are also useful. For example, to attach tendon to bone, the bone phase preferably contains 45S Bioglass® ceramic, which "binds" hard connective tissue such as cementum or bones, and the tendon phase preferably contains Bioglass® ceramic, which interacts with both hard and soft connective tissue such as tendon or ligament. Alternatively, a single phase implant may be used, containing 55S Bioglass® ceramic, which interacts with both hard and soft tissue. In another embodiment of this invention, composite material may be used in particulate form to enhance periodontal repair where regeneration of cementum (hard tissue), periodontal ligament (soft tissue) and bone (hard tissue) is necessary. The porous nature of the implant permits the use of marrow, which contains wound healing cells, or other cells of interest.

Implant materials of this invention which are substantially non-porous (also referred to herein as "fully dense" or "solid") are preferably used for fracture fixation devices such as plates, screws and rods. The Young's modulus of nonporous materials of this invention, tested under physiological conditions, should be between about 1 GPa and about 100 GPa when tested using the dynamic mechanical analysis three point bending test as described herein. The moduli specified herein are understood to be as so tested. For application to cancellous bone and partial weight-bearing areas of bone, the Young's modulus is preferably between about 1 GPa and about 30 GPa. For application to full weight-bearing areas of bone, the Young's modulus is preferably between about 5 GPa and about 30 GPa. In addition to providing increased mechanical properties to nonporous implant materials, the presence of bioactive ceramic in the material of bone fixation devices such as screws improves the ability of the implant to cut into the bone as it is drilled into place.

The bioactive ceramic (preferably Bioglass®), should be present in porous implant materials in an amount less than about 40 volume percent, and preferably less than about 30 volume percent, down to about 10 volume percent. The bioactive ceramic should be present in nonporous implant materials in an amount of about 10 volume percent to about 70 volume percent, preferably no more than about 50 to 60 volume percent.

Bioactive ceramics are known to the art as discussed above, and include, as preferred species for use in this invention, 45S, 55S, and 65S Bioglass® particles having a particle size of 90–53 $\mu$m, or a particle size of 53–38 $\mu$m, or alkali free sol-gel Bioglass® particles. The 65S Bioglass® product is non-active, i.e., fits under the definition of surface-passivated materials as used herein; however the sol-gel 65S Bioglass® product is surface-active. The bioactive ceramic may be used in a variety of shapes, such as irregular-shaped particles, fibers and particles having controlled geometrical shapes.

In a preferred embodiment, the bioactive ceramic is surface-passivated, as applicants have discovered, surprisingly, that under wet physiological conditions, the moduli (storage modulus and Young's modulus) of the implant containing bioactive ceramic decrease compared to the moduli measured under dry conditions. This problem is solved by passivating the surface of the bioactive ceramic (mating it non-reactive to water). The term "surface-passivated" herein thus means that the surface of the bioactive ceramic in the polymeric composite material has been made incapable of reacting with water, preferably by pre-reacting with water to form an apatitic layer. Alternatively, the bioactive ceramic particles may be coated with a polymeric film, as by dispersing them in a weak solution of polymer and drying, before incorporation into the polymer. This alters the surface of the bioactive ceramic to allow better bonding of the polymer but does not prevent further bioactivity of particle surfaces exposed to the aqueous environment when implanted. For example, pre-reacting forms a slight apatite layer which will interfacially bond with the polymer phase, but in a prepared implant, the surface of the bioactive ceramic exposed to the body still reacts to form the interfacial bond.

In an alternative embodiment of this invention, a silane coupling agent is added to the composite material to passivate the surface of the bioactive material and strengthen the interface between the polymer and the bioactive ceramic. An amount of such coupling agent sufficient to coat the surface of the particles used is an effective amount.

Bioactive ceramic materials which are not surface-passivated and which do react with water are called "surface-active" materials herein. In one embodiment of this invention, both surface-active and surface-passivated materials are incorporated into the biodegradable polymeric material. Since these two types of bioactive ceramic have different effects on mechanical properties, the ratio of surface-active to surface-passivated material may be varied to achieve desired mechanical properties in the finished implant material while maintaining a desired total bioactive ceramic content.

Composite therapeutic implant materials of this invention comprising surface-passivated bioactive ceramic have enhanced (greater) mechanical properties both when compared to such compositions containing non-surface-passivated bioactive ceramics and to such compositions containing no bioactive ceramics. Mechanical properties are described herein in terms of Young's modulus and storage modulus. Young's modulus may be measured by means known to the art. With respect to the studies of materials of this invention reported herein, Young's modulus has been found to be about an order of magnitude less than storage modulus.

Composite materials of biodegradable polymers and bioactive ceramics are also effective to buffer the pH of the environment of an implant made with the material as the implant degrades so as to avoid potentially deleterious effects of acidic degradation products.

The applicants have also discovered that the addition of bioactive ceramic particles in making porous biodegradable polymers decreases the molecular weight and glass transition temperature of the implant, which can influence the degradation time of the implant. Accordingly, methods of making porous biodegradable polymeric implant materials comprising bioactive ceramics are provided which take into account these effects and allow selection of appropriate starting materials with appropriate molecular weights to provide finished implants of selected molecular weights, degradation times, storage moduli, or Young's moduli and glass transition temperatures. In porous implant materials, addition of bioactive ceramic decreases the molecular weight of the material about 1 percent per percent of bioactive ceramic added.

Methods of using the materials of this invention for accelerated healing of defects in bone and other tissue are also provided.

Biodegradable polymeric cylinders, wafers, spheres, strips, films, and irregularly-shaped implants, as well as particulate bone-graft materials containing bioactive ceramics are provided herein, as are biodegradable polymeric hand-shapable materials containing bioactive ceramics and biodegradable polymeric materials capable of continuous, smooth release of bioactive agents and containing bioactive ceramics.

The term "biodegradable" means capable of breaking down over time inside a patient's body or when used with cells to grow tissue outside of the body. A therapeutic implant is a device used for placement in a tissue defect in a patient (human or animal) to encourage ingrowth of tissue and healing of the defect. Composite implants of this invention may comprise cells.

Polymers known to the art for producing biodegradable implant materials may be used in this invention. Examples of such polymers are polyglycolide (PGA), copolymers of glycolide such as glycolide/L-lactide copolymers (PGA/PLLA), glycolide/trimethylene carbonate copolymers (PGA/TMC); polylactides (PLA), stereocopolymers of PLA such as poly-L-lactide (PLLA), Poly-DL-lactide (PDLLA), L-lactide/DL-lactide copolymers; copolymers of PLA such as lactide/tetramethylglycolide copolymers, lactide/trimethylene carbonate copolymers, lactide/δ-valerolactone copolymers, lactide ε-caprolactone copolymers, polydepsipeptides, PLA/polyethylene oxide copolymers, unsymmetrically 3,6-substituted poly-1,4-dioxane-2,5-diones; poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolatone, poly-ε-caprolactone, methylmethacrylate-N-vinyl pyrrolidone copolymers, polyesteramides, polyesters of oxalic acid, polydihydropyrans, polyalkyl-2-cyanoacrylates, polyurethanes (PU), polyvinyl alcohol (PVA), polypeptides, poly-β-maleic acid (PMLA), and poly-β-alkanoic acids.

Preferred biodegradable polymers for use in making the materials of this invention are known to the art, including aliphatic polyesters, preferably polymers of polylactic acid (PLA), polyglycolic acid (PGA) and mixtures and copolymers thereof, more preferably 50:50 to 85:15 copolymers of D,L-PLA/PGA, most preferably 55/45 to 75:25 D,L-PLA/PGA copolymers. Single enantiomers of PLA may also be used, preferably L-PLA, either alone or in combination with PGA.

Preferably the polymeric implant material has a molecular weight between about 25,000 and about 1,000,000 Daltons, more preferably between about 40,000 and about 400,000 Daltons, and most preferably between about 55,000 and about 200,000 Daltons.

Also provided is a biodegradable film for application to a wound in a patient comprising a biodegradable polymer and between about 10 and about 70 percent of a bioactive ceramic. This invention also teaches methods of making porous composite therapeutic implant materials comprising bioactive ceramic and biodegradable polymer comprising preparing said polymer in uncured form, mixing a bioactive ceramic into said polymer, placing said mixture into a mold and curing under vacuum pressure conditions to produce the porous composite implant material.

Methods of making substantially nonporous composite therapeutic implant materials are also taught, comprising preparing said polymer in uncured form, mixing a bioactive ceramic into said polymer, and curing said mixture under conditions of heat and pressure to produce a substantially nonporous composite implant material.

The composite implant materials of this invention may be used by forming said materials into implant devices selected from the group consisting of: tissue scaffolds with and without cells, granular bone graft substitute material, two-phase osteochondral implants, weight-bearing bone implants, tacks, pins, screws, bone onlays, and films.

Preferably the polymeric implant material is capable of maintaining a pH between about 6 and about 9 in a physiological environment, and more preferably between about 6.5 and about 8.5

DETAILED DESCRIPTION OF THE INVENTION

The composite therapeutic implant materials of this invention are made by incorporating the bioactive ceramic into the polymeric material prior to curing the material. Applicants have found the processing stage at which the bioactive ceramic is added does not appear to make a difference in the properties of the final product.

The preparation of precipitated polymers is well known to the art. In general, the process comprises mixing a dried polymer mix with an art-known solvent such as acetone, methylene chloride or chloroform, preferably acetone, precipitating the polymer mass from solution with a non-solvent, e.g. ethanol, methanol, ether or water, extracting solvent and precipitating agent from the mass until it is a coherent mass which can be rolled or pressed into a mold, or extruded into a mold, and curing the composition to the desired shape and stifffness. Porous composite materials of this invention are made as described in U.S. Patent application Ser. No. 08/727,204, incorporated herein by reference, with bioactive ceramic added to the polymer before curing. Nonporous (fully dense) composite materials of this invention may be made, as described herein, by mixing particles of polymer and bioactive ceramic and subjecting to pressure in a heated press.

This invention provides porous or nonporous biodegradable implant materials. Porous implants are especially useful for providing scaffolds for tissue ingrowth or as carriers of cells. Nonporous implants are especially useful for load-bearing applications. Porous implant materials preferably have a porosity between about 60 and 90 volume percent wherein the pore size distribution throughout the material is substantially uniform. The target porosity of the materials of this invention is achieved by adding more or less polymer to the mold. For example, in preparing N number of molded wafers to have a selected target porosity Q, in a mold having a length a (mm), a width b (mm) and a depth c (mm), using a polymer of density p (g/cm$^3$), the mass of polymer M to be used is calculated by:

$$M = \frac{a \cdot b \cdot c}{1000} p(1-Q)N.$$

The porous implant materials of this invention preferably have an average pore size of between about 5 $\mu$m and about 400 $\mu$m, more preferably between about 100 $\mu$m and about 200 $\mu$m. Porous materials preferably contain no more than about 40 volume percent Bioglass® ceramic, more preferably no more than about 20 to 30 volume percent Bioglass®ceramic. Nonporous implants can contain up to about 70 volume percent Bioglass® ceramic.

The implant material may incorporate cells, bioactive agents as known to the art, or other additives known to the art such as matrix vesicles or matrix vesicle extracts as described in U.S. patent application Ser. No. 08/250,695, incorporated herein by reference. Implant materials of this invention may include channels to facilitate tissue ingrowth, and may be infiltrated with nutrient and/or cellular material such as blood and narrow cells, cartilage cells, perichondrial cells, periosteal cells, and other cells of mesenchymal origin, e.g., osteoblasts, chondrocytes, and their progenitors, adipocytes, muscle cells, tendon cells, ligament cells, dermal cells and fibroblasts, to facilitate tissue growth. The implant materials of this invention may also incorporate bioactive agents such as enzymes, growth factors, degradation agents, antibiotics and the like, designed for release over time, as described in U.S. patent application Ser. No. 08/196,970 incorporated herein by reference.

For best biocompatibility it is preferred that the implant material be substantially free of solvent. It is recognized that some residual solvent will be left in the polymer, but preferably less than about 100 ppm.

The implant materials of this invention may be used to make multi-phase implants such as the two-phase implants as described in PCT publication WO 93/15694, incorporated herein by reference. These two-phase implants preferably have an upper cartilage phase and a lower bone phase and are inserted into a defect extending from cartilage into bone with the appropriate phases adjacent the same tissues. The implant materials hereof may be made in the form of three-dimensional porous scaffolds for ingrowth of tissue, e.g. cylinder-shaped implants as disclosed in WO publication 93/15694, modified in accordance with the teachings hereof to contain bioactive ceramics.

The implant materials hereof may also be used to make biodegradable polymeric films as disclosed in co-pending application Ser. No. 60/032,085, also incorporated herein by reference, modified in accordance with the teachings hereof to contain bioactive ceramics. Such films may be used for surgical attachment of muscles, as for ocular implants where the surgeon may suture through the film for muscle attachment, and may be porous or nonporous, preferably nonporous.

Such films may be made by dissolving the selected polymeric material in a solvent known to the art, e.g. acetone, chloroform or methylene chloride, using about 20 ml solvent per gram of polymer. The solution is then degassed, preferably under gentle vacuum to remove dissolved air and poured onto a surface, preferably a flat non-stick surface such as Bytac (Trademark of Norton Performance Plastics, Akron, Ohio) non-stick coated adhesive-backed aluminum foil, glass or Teflon. The solution is then dried, preferably air-dried, until it is no longer tacky and the liquid appears to be gone. The known density of the polymer may be used to back-calculate the volume of solution needed to produce a film of the desired thickness.

To make the film biocompatible, residual solvent which interferes with cell implantation must be removed. Preferably this is done by incubating the dried polymer at about 55–65° C. to drive off residual solvent. A vacuum oven may then be used at about 55–70° C. to remove the final solvent, so that the finished polymeric film has a residual solvent concentration of less than about 100 ppm. The film is then peeled away from the non-stick surface, and is substantially uniform in thickness, smooth, tough, and durable.

Films may also be made by heat pressing and melt forming/drawing methods known to the art. For example, thicker films can be pressed to form thinner films, and can be drawn out after heating and pulled over forms of the desired shapes, or pulled against a mold by vacuum pressure.

To create films to which bone and soft tissue will attach on only one or both sides, a film can be either heat-pressed or cast for a solvent (e.g., chloroform, acetone or methylene chloride) and allowed to cure at least partially. While still tacky, a layer of bioactive ceramic particles can be applied to the desired thickness or surface density. Preferably, non-surface-passivated particles are used. Alternatively, the surface of a prefabricated film can be softened and the particles applied.

Shapable materials as disclosed in copending application Ser. No. 08/727,204 and the corresponding PCT application incorporated herein by reference, modified to contain Bioglass® are also provided by this invention as well as materials providing continuous smooth release of bioactive agents as disclosed in co-pending application Ser. No. 08/196,970 incorporated herein by reference, modified to contain bioactive ceramics.

The incorporation of bioactive ceramics into biodegradable polymeric materials as disclosed herein, preferably in an amount between about 10 and about 70 volume percent, increases the mechanical properties of the material as measured under physiological conditions in terms of storage modulus or Young's modulus. Storage modulus is measured on cut bars of punched round samples of polymeric wafers using three-point bending on a Perkin Elmer 7 Series Thermal Analysis System. Young's modulus is considered herein to be about an order of magnitude less than storage modulus.

As is known to the art, the lifetime of the material in vivo may be increased by increasing the amount of D,L-PLA or L-PLA content, molecular weight and degree of crystallinity, or decreased by decreasing the same factors. It has been found, unexpectedly, for porous materials that addition of bioactive ceramics may also decrease the molecular weight, and therefore decrease the degradation period.

To make the polymer/bioactive ceramic compositions of this invention, a suitable polymeric material is selected, depending on the degradation time desired for the implant material. Selection of such polymeric materials is known to the art. For example PLA is used when a lengthy degradation time is desired, e.g. up to about two years. A low target molecular weight, e.g., around 20,000 daltons, 50:50 or 55:45 PLA:PGA copolymer is used when an approximately two-week degradation time is desired. To ensure a selected target molecular weight, degradation time, the molecular weights and compositions may be varied as known to the art and taught herein depending on the mass of the implant formed from the polymer/bioactive ceramic composition.

The degradation of PLA and PGA has been extensively studied, both in vivo and in vitro. A number of factors affect the degradation rate of PLA:PGA copolymers, such as molecular weight, copolymer ratio, polymer crystallinity, thermal history, shape and porosity, and wettability. Additionally, other factors such as anatomical site of implant, vascularity, tissue interaction and patient response affect the degradation rate in vivo. Depending on the above listed factors, degradation times for PLA and PGA polymers have been reported as low as 7 days for 50:50 PLG to several years for PLA. The overall degradation kinetics have been fairly well established for the entire family of homopolymers and copolymers. Table 1, below, summarizes the findings of the degradation rates of the copolymers. Since this table is a compilation of many studies, the broad degradation range is reflective of the different experimental variables and parameters utilized.

TABLE 1

Degradation rates of polymers

| PLA/PGA | Degradation Time |
|---|---|
| 100/0 | 24 weeks-over 4 years |
| 85/15 | 12–34 weeks |
| 75/25 | 4–20 weeks |
| 70/30 | 25–30 weeks |
| 50/50 | 1–8 weeks |
| 0/100 | 8–20 weeks |

It is preferred that implant materials of this invention have a glass transition temperature (Tg) between about 38° C. and about 50° C. It has been discovered by applicants that incorporation of bioactive ceramics decreases the glass transition temperature of porous composite materials.

Bioactive ceramics may be added to polymeric films as described in U.S. patent application Ser. No. 60/032,085, incorporated herein by reference.

The following examples illustrate embodiments of this invention but are not intended to limit the scope thereof. Those skilled in the art will understand that a number of different polymers, reagents, bioactive ceramics, and processing conditions may be substituted for those specifically exemplified to provide equivalent results, all of which are intended to be encompassed within the scope of the claims hereof.

EXAMPLES

Example 1

Method of Making Porous Polymeric Wafers Not Containing Bioglass®.

Five grams of PLA/PGA (75:25) polymer, molecular weight 80,000 D, intrinsic viscosity about 0.6 to about 0.75 in chloroform, were weighed into a Teflon beaker. A ¾" Teflon-coated magnetic stirring bar was placed in the beaker and the beaker placed on a magnetic stirplate. 30 ml acetone was added and the mixture stirred (at setting 8 on the stirplate) for about 20 minutes until the polymer was completely dissolved. Polymer was precipitated by adding 30 ml ethanol and stirring for about 20 seconds (at setting 3 on the stirplate) to agglomerate the polymer gel mass.

The supernatant liquid was then decanted and the gel mass turned onto a Teflon plate to be used as a work surface. The stirbar was separated from the mass by using a Teflon policeman, recovering as much polymer as possible. Excess liquid was blotted away using care not to touch the polymer with the Kimwipe blotter. The polymer mass was then rolled and flattened to a thin sheet (1±0.1 mm thick) using a bar of round Teflon stock about ¾" in diameter.

The Teflon plate with the polymer was then placed in a vacuum desiccator, and vacuum was applied for several minutes (2 to 4.5 min) using a KNF reciprocating diaphragm vacuum pump until the polymer mass became blistered and bubbly as the solvent was removed. The vacuum was released and the Teflon plate with the polymer was removed from the desiccator. Using rubber gloves, the polymer gel was hand-rolled into a ball and kneaded using thumbs and forefingers until the material became soft and extensible. During this process a small amount of residual solvent was released and the polymer felt slightly wet. Kneading was continued until no more liquid was evident. The gel was then rolled out into a thin sheet using the Teflon bar and being careful not to allow the polymer to wrap around the bar, as the polymer at this point was quite sticky and readily adhered to itself upon contact.

The polymer was then again placed in the desiccator and vacuum was applied for several more (2 to 4.5) minutes until the gel expanded and appeared "foamy," having many fine bubbles distributed throughout the matrix. The polymer was removed from vacuum and again kneaded as before until it was soft and extensible and took on the lustre of spun sugar and a "satiny" appearance. The mass of the polymer gel at this point was recorded.

The polymer gel was then divided into five equal pieces, and the pieces were shaped to fit the well of a mold. The mold was wafer-shaped, approximately 20 mm×40 mm×3 mm, and perforated with holes having a 0.7 mm diameter spaced approximately 3 mm to 10 mm apart. Care was taken to shape each piece to fit the well of the mold, making sure that the surface was uniform and even with no thin spots and that the material filled the mold edge to edge. The molds (without top) were then placed into the desiccator and vacuum (100 mTorr) was applied for two minutes. The molds were then removed from the desiccator and the tops of the wafers flattened without completely compressing the expanded polymer. The top plates of the molds were then affixed using appropriate nuts and bolts.

The molds were then placed in a vacuum oven at 60–65° C. under vacuum of less than 50 mTorr for 24–48 hours. For cartilage phase materials, i.e. wafers having mechanical properties of cartilage, the treatment vacuum oven was continued at the same temperature for an additional 24 hours. After curing, the polymer was substantially free of solvent.

The resulting polymeric cartilage phase wafers were uniform in porosity, having an average pore size of about 100 μm and a percent porosity of about 65 volume percent. They were flexible and, when slightly warmed in the hand to about body temperature, were easily hand-shapable.

The resulting polymeric bone phase wafers were also uniform in porosity, having an average pore size of about 150 μm and a percent porosity of about 70 volume percent. Although they were not as flexible as the cartilage phase wafers at room temperature, they could be hand-shaped at body temperature.

Example 2

Method of Making Fully-Dense Bioglass®/PLG Composites.

The selected polymer (75/25 PLG) was ground in a blender and sieved to a particle size of <20 mesh (<850 μm). The material was then weighed into the stainless steel bowl of the blender and the appropriate amount of Bioglass® added to provide a 10 volume percent Bioglass® composition. To determine the relative volume fraction to weight fraction, the following equation was used:

$$f_v = \frac{\frac{x}{\rho_{BG}}}{\frac{x}{\rho_{BG}} + \frac{1-x}{\rho_{PLG}}}$$

WHERE:
$f_v$=Volume fraction of Bioglass®
x=Weight fraction of Bioglass®
$\rho_{BG}$=Density of Bioglass®
$\rho_{PLG}$=Density of PLG The blender was then pulsed briefly 3 or 4 times to thoroughly combine the two materials. Excessive blending is avoided at this point to prevent abrading the surface of the blender bowl, which results in discoloration of the finished product.

The combined material was then transferred to a pressing cylinder, the platens of which were lined with aluminum foil disks. The assembled cylinder (with pistons in place) was then transferred to a Carver heated press. The heating platens were adjusted to a power level of "1," producing a surface temperature of about 240° F. (~115° C.). A load of 20,000 pounds (about 5000 psi) was applied and the mold allowed to come to a temperature of 85–95° C., measured at the external surface of the cylinder.

Once temperature was reached, the load was re-adjusted to 20,000 pounds, the power to the platens turned off, and cooling water applied. The temperature was allowed to fall to below 40° C. before being removed from the press. The part was then removed and the aluminum foil disks removed.

The process was repeated to make a composite material containing 20 volume percent Bioglass® ceramic.

The foregoing steps were repeated using 55/45 PLG.

Example 3

Bioglass® Ceramic Concentration Studies

Experiments were conducted to determine the maximum amount of Bioglass® ceramic which should be incorporated into porous polylactide-co-glycolide/Bioglass® composites of this invention.

Wafers 20×40×3 mm wafers having target porosities of 70% were manufactured using 55/45 D,L-PLG (55 percent poly-d,l-lactic acid copolymerized with 45 percent polyglycolic acid), according to procedures described in Example 1, modified by adding 30, 40 and 50 volume percent Bioglass® ceramic. The polymer was Birmingham Polymer, Inc. Lot #D96012 55/45 D-PLG having an intrinsic viscosity of 0.85. The Bioglass® ceramic was 45S5 Bioglass® powder having an average particle size of 53–38 μm as determined by scanning electron microscopy and laser-light scattering techniques. Solvents used were Fisher Optima Grade acetone and Quantum 100% anhydrous ethanol.

Differential Scanning Calorimeter (DSC): To determine the glass transition temperature, differential scanning calorimetry was performed using a Mettler DSC 12-E with a first run of –5 to 250° C. at a rate of 10° C./min and a second run of –5° to 100° C. at a rate of 10° C./min. For analysis, the glass transition Tg) onset from Run 2 of the various samples were compared for each composition. As the amount of Bioglass® ceramic increased in the samples, the Tg decreased. The results indicate that the Run 2 Tg onset decreased from 39.0° C. for 30 volume percent Bioglass® to 36.4° C. for 40 volume percent Bioglass® in 55/45 PLG. These results seem to indicate that the decrease in Tg is related to the decrease in molecular weight. DSC results of the composition containing 50 volume percent Bioglass® ceramic showed no recognizable exo/endothermic peaks on the plots probably due to the high amount of Bioglass® ceramic.

High Performance Liquid Chromatography (BPLC): To determine the molecular weight of the polymer wafers, high performance liquid chromatography (HPLC) was run using tetrahydrofuran (THF) as the solvent, with a 0.80 ml/min flowrate. Fifty microliters were injected into a TosoH TSK-GEL 4000+3000 column at a concentration of 10.820 mg/ml with a column and detector temperature of 25° C. The data shows there was a significant decrease in molecular weight (Mw). The 30 volume percent Bioglass® composition showed a 3.5 fold decrease in Mw, the 40 volume percent composition showed a 4.2 fold decrease, and the 50 volume percent composition showed an 8.8 fold decrease.

Gas Chromatography: To determine the residual acetone and ethanol levels, gas chromatography was performed using Hewlett Packard 6890 and running a FID protocol with nitrogen as the carrier gas. The results show that residual acetone levels for the PLG Plus Bioglass® wafers were below the 100 ppm detection limit.

These results showed that compositions containing up to 40 volume percent Bioglass® ceramic can be added to the polymer with a good wafer resulting. The addition of fifty volume percent Bioglass® ceramic to the polymer resulted in a wafer that was difficult to knead, did not filly expand into the molds, and had uneven porosity. Bioglass® ceramic decreases the molecular weight and concurrently its Tg in porous implant materials.

Example 4

Order of Process Steps.

Experiments were conducted to determine the effect of adding Bioglass® ceramic at various steps of polymer processing.

Wafers 20×40×3 mm with target porosities of 70% were made using 55/45 D,L-PLG from Birmingham Polymers, Inc. (Lot D96012), having an intrinsic viscosity of 0.85, molecular weight (raw polymer) of about 72,233, and a glass transition temperature measured under conditions set forth in Run 2 of Example 2 above, of about 43.0° C. The Bioglass® ceramic used was 45S5 Bioglass® ceramic powder having an approximate particle size of 90–53 μm, as determined by scanning electron microscopy and laser-light scattering techniques. Bioglass® ceramic was added to form a polymer/Bioglass® ceramic composition containing 20 volume percent Bioglass® ceramic.

Solvents and procedures used were as described in Example 2, with the exception that Bioglass® ceramic was added at different points in the procedure as follows:

Group A: Added Bioglass® ceramic at start of dissolution (mix Bioglass® ceramic in with PLG and acetone)

Group B: Added Bioglass® ceramic to dissolved polymer solution prior to precipitation Group C: Added Bioglass® ceramic to precipitated mass prior to first vacuum step Group D: Added Bioglass® ceramic to precipitated mass prior to second vacuum step Group E: Added Bioglass® ceramic to precipitated mass prior to third vacuum step Addition of Bioglass® ceramic to the polymer was successful for all five treatment groups. As before and in this experiment, when adding Bioglass® ceramic to the precipitated polymer mass (Groups C, D, and E) there was a slight, probably insignificant loss of Bioglass® ceramic which occurs when the polymer mass becomes dry and tears during kneading. On the contrary, for Groups A and B the Bioglass® ceramic was easily dissolved in the polymer/acetone mixture which resulted in an easier transfer of precipitated polymer mass and insured a 100% incorporation of the Bioglass® ceramic to the polymer.

After processing, polymer wafers were placed under vacuum at 50° C. for 4 days (2 days in the mold and 2 days in a Petri dish) to allow ample time for removal of residual solvents. To verify residual solvent content and to measure as-processed Mw, Tg, GC, DSC, and HPLC were run on one sample from each treatment group.

The following standard quality control tests were run on one sample from each treatment group:

GC: Run on one sample per treatment group to confirm acceptable (below 100 ppm) residual solvent levels HPLC: Run on one sample per treatment group to determine Mw of processed sample DSC: Run on one sample per treatment group to determine Tg of processed sample.

Differential Scanning Calorimetry: To determine the glass transition temperature, differential scanning calorimetry (DSC) was performed using a Mettler DSC 12-E with a first run of –5° C. to 250° C. at a rate of 10° C./min and a second run of –5 to 100° C. at a rate of 10° C./min. For analysis, the Tg onsets from Run 2 of the various samples were compared for each treatment group (Table 2). Overall, the average Tg onset from Run 2 of the five groups was 40.0 plus or minus 0.5° C. A one-way ANOVA ($p<0.05$ significance level) of the Run 2 Tg onset resulted in a p-value of 0.28, which indicates there is no statistically significant difference between the Run 2 Tg onset of the five treatment groups.

High Performance Liquid Chromatography: To determine the molecular weight of the polymer wafers, high performance liquid chromatography (HPLC) was run using tetrahydrofuran (THF) as the solvent, with a 0.80 ml/min flowrate. Fifty microliters were injected into a TosoH TSK-GEL 4000+3000 column at a concentration of 10.820 mg/ml with a column and detector temperature of 25° C. The Mw values for the five treatment groups ranged between 61,000 and 69,900 Da. Table 3 shows the values for each group, with the overall average Mw being 64,650 plus or minus 3044 Da. A one-way ANOVA ($p<0.05$ significance level) resulted in a p-value of 0.08, which indicates there is no statistically significant difference between the Mw of the treatment groups.

Gas Chromatography: To determine the residual acetone and ethanol levels, gas chromatography was performed using Hewlett Packard 6890 and running a FID protocol with nitrogen as the carrier gas. Results indicate that none of the groups contained any residual ethanol. Groups A, B, and C contained no detectable residual acetone whereas Groups C and D contained below 100 ppm acetone. This indicates that the addition of Bioglass® ceramic at various steps does not affect the loss of residual acetone and ethanol.

These results indicate that the addition of Bioglass® ceramic at various steps in the manufacturing of polylactide-co-glycolide wafers does not significantly alter the chemical properties of the wafer. The addition of Bioglass® ceramic to the polymer resulted in acceptable wafers for all five groups. Statistical analysis showed that there is no significant change of Tg onset for Run 2 or the Mw in the five groups despite the addition of Bioglass® ceramic at different points in the polymer processing.

Because there was no significant alteration in chemical properties of the wafers in the different treatment groups, mechanical testing was not done.

Example 5

Mechanical Properties, Molecular Weight and Glass Transition Temperature of Porous Bioglass® Ceramic/Polymer Compositions Wafers were manufactured as in Example 2 using: (A) 55/45 D,L-PLG from BPI having a molecular weight of about 72,233, an intrinsic viscosity of about 0.85 (HFIP 30° C.) and a glass transition temperature of about 43° C., having 5, 10 and 20 volume percent Bioglass® ceramic M (45S powder, having an approximate particle size of 90–53 μm as determined by scanning electron microscopy and laser-light scattering techniques); (B) 65/35 D,L-PLG having a molecular weight of about 77,400, an intrinsic viscosity of 0.86 (HFIP 30° C.) and a glass transition temperature of about 41.9° C., having 5, 10 and 20 volume percent Bioglass® ceramic); and (C) 75/25 D,L-PLG having a molecular weight of about 90,300, an intrinsic viscosity of about 0.76 (chloro, 25° C.) and a glass transition temperature of about 48.4° C., having 5, 10 and 20 volume percent Bioglass® ceramic. Wafers 20×40×3 mm and 60×60×3 mm were made with 70 percent target porosity. After making, wafers were placed under vacuum at 50° C. for four days (two days in the mold and two days in a Petri dish) to allow ample time for removal of residual solvents.

Wafers were visually examined to determine manufacturing success, and the following standard quality control tests were run:

GC: One sample run from a 20×40×3 mm wafer and a 60×60×3 mm wafer per treatment group to confirm acceptable (below 100 ppm) residual solvent levels;

BPLC: One sample run per treatment group to determine Mw of processed sample;

DSC: One sample run per treatment group to determine Tg of processed sample;

DMA: One bar from an end region and one bar from the center region of two 20×40×3 mm wafers with dimensions (width, height, length) of 4×3×20 mm were carefully cut for DMA testing using a scalpel. Four bars were run from two 20×40×3 mm wafers. Three-point bend tests were run using dry material from 0 to 70° C. Data were plotted to indicate both storage and loss moduli.

Porosity: Pore size distribution and porosity were determined using mercury intrusion porosimetry.

pH change: Change in pH was measured over time.

Figure 1:
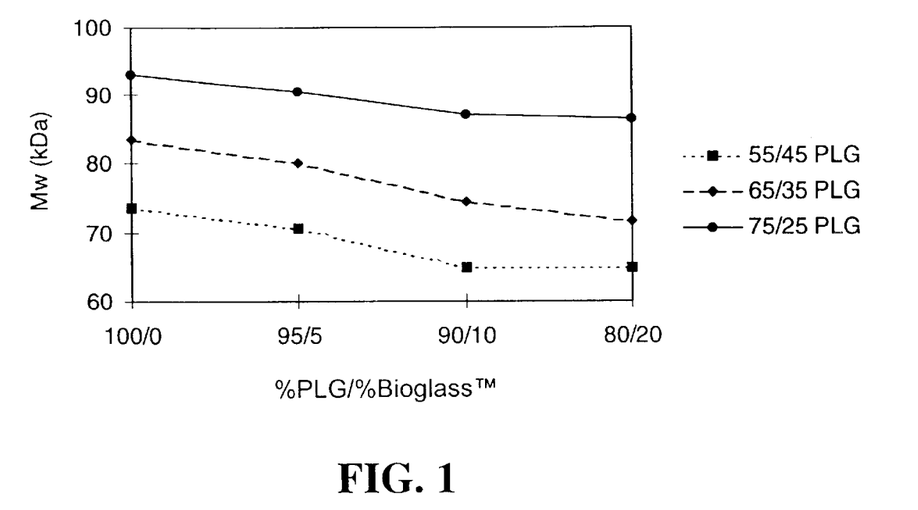
FIG. 1 shows decreasing molecular weight of porous Bioglass®/polymer compositions comprising 55/45, 65/35 and 75/25 PLG as a function of increasing Bioglass® ceramic concentration from 5 volume percent to 20 volume percent.
Figure 2:
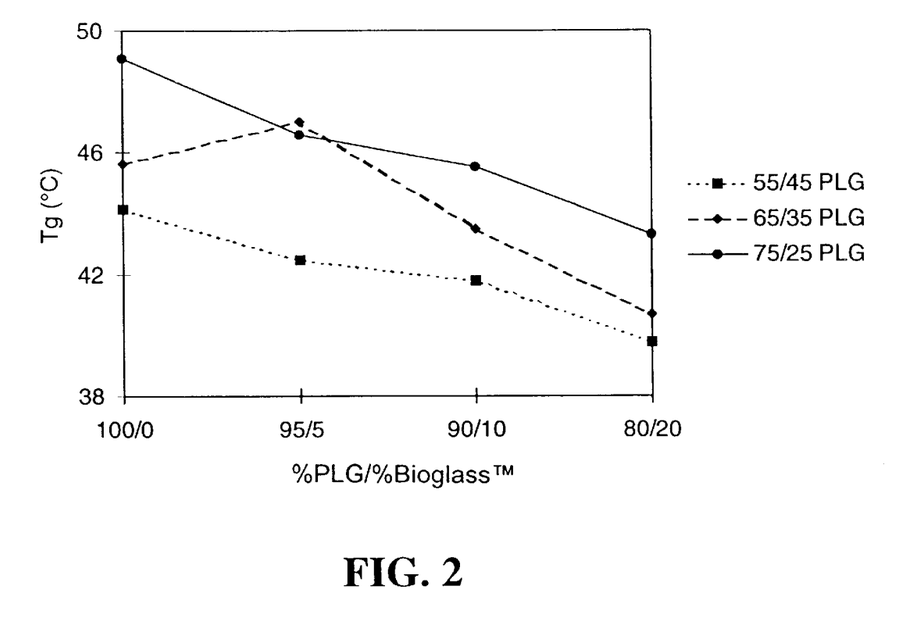
FIG. 2 shows decreasing glass transition temperatures of porous Bioglass® ceramic/polymer compositions comprising 55/45, 65/35 and 75/25 PLG as a function of increasing Bioglass® ceramic concentration from 5 volume percent to 20 volume percent, tested dry.
Figure 3:
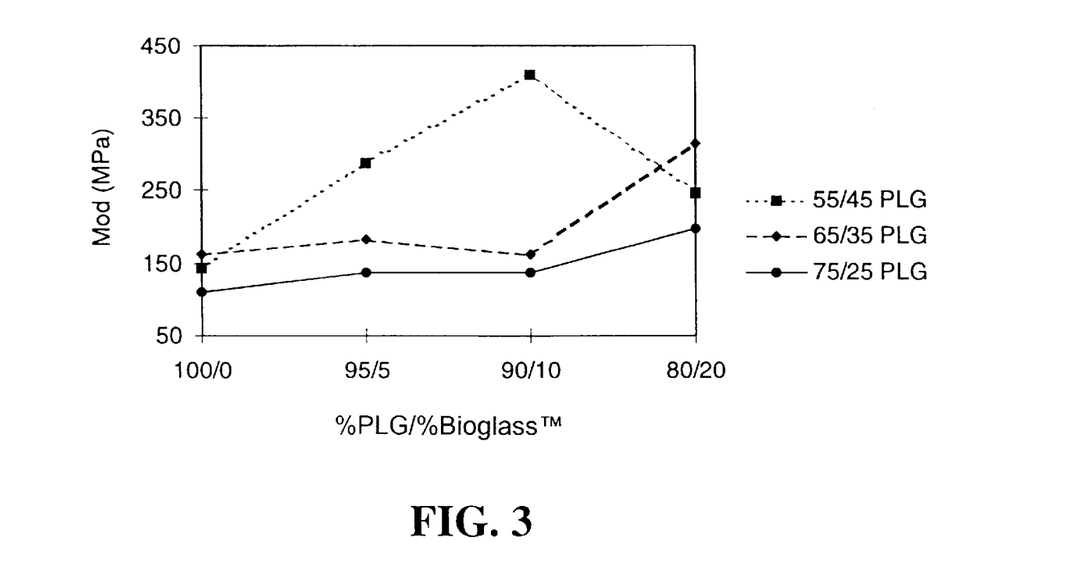
FIG. 3 shows variation of mechanical properties (storage modulus at 37° C., dry) of porous Bioglass® ceramic/polymer compositions comprising 55/45, 65/35 and 75/25 PLG as a function of increasing Bioglass® concentration from 5 volume percent to 20 volume percent.

The treatment groups were as follows:
1. Control A: 100% PLG (55/45 DL)
2. Group A1: PLG (55/45 DL)+5 v/% Bioglass® ceramic
3. Group A2: PLG (55/45 DL)+10 v/% Bioglass® ceramic
4. Group A3: PLG (55/45 DL)+20 v/% Bioglass® ceramic
5. Control B: 100% PLG (65/35 DL)
6. Group B1: PLG (65/35 DL)+5 v/% Bioglass® ceramic
7. Group B2: PLG (65/35 DL)+10 v/% Bioglass® ceramic
8. Group B3: PLG (65/35 DL)+20 v/% Bioglass® ceramic
9. Control C: 100% PLG (75/25 DL)
10. Group C1: PLG (75/25 DL)+5 v/% Bioglass® ceramic
11. Group C2: PLG (75/25 DL)+10 v/% Bioglass® ceramic
12. Group C3: PLG (75/25 DL)+20 v/% Bioglass® ceramic Results are shown in FIGS. 1–3.

Mechanical Testing: Dynamic mechanical analysis (DMA) was done on cut bars of the polymer wafer using three-point bending on a Perkin Elmer 7 Series Thermal Analysis System. Bars from the center and the end region of the wafers were tested as described above. The bars were exposed to 0–70° C. at a rate of 5° C./min. The storage and loss moduli were measured and plotted. From the modulus vs. temperature plot, the maximum storage modulus, the storage modulus at 37° C., the temperature at maximum loss modulus, and the temperature at 50% drop of the storage modulus were determined.

Data were tabulated and statistical analysis was performed to determine if there were any significant differences between the storage modulus at 37° C. of the two regions (end and center) and the four treatments (0, 5, 10 and 20 v/% addition of Bioglass® ceramic) within each polymer group. A two-way analysis of variance, specifically a Tukey all pairwise multiple comparison test (p-value of <0.05 considered significant) was utilized. The storage modulus at 37° C. from the center region and end regions showed no significant differences for any of the three polymer groups (p=0.59 for 55/45, p=0.25 for 65/35, p=0.12 for 75/25). Since no significant difference could be found between end and center regions, DMA results for each treatment group were grouped together. For each polymer group (A, B, C), there was a noticeable increase in maximum storage modulus and storage modulus at 37° C. as Bioglass® ceramic content increased. The moduli increase was largest for Group A with the least increase for Group C.

Groups A and B of this experiment were compared to the values from Example 2 using a Bioglass® ceramic particle size range of 53–38 μm as compared to 90–53 μm for this experiment. Of the eight groups compared, only two groups having smaller particle size had larger values for maximum storage modulus and storage modulus at 37° C. Also, only one group having the smaller particle sizes had higher temperatures at maximum loss modulus and at 50% storage modulus than the similar groups having a larger particle sizes and one group having the smaller particle sizes had higher temperature at maximum loss modulus. These results indicate that the added Bioglass® ceramic with larger particle sizes has a more profound effect on the mechanical properties of the wafer than the Bioglass® ceramic with smaller particle sizes.

Differential Scanning Calorimetry: To determine the glass transition temperature, differential scanning calorimetry (DSC) was performed using a Mettler DSC 12-E with a first run of −5° to 250° C. at a rate of 10° C./min and a second run of −5° to 100° C. at a rate of 10° C./min. For analysis, the Tg onset from run 2 of the various samples were compared for each treatment group. Groups A3, B3, and C3 (20 v/% Bioglass® ceramic) resulted in a decrease in the Run 2 Tg onset of 4.3°, 4.9°, and 5.8°, respectively, from the control groups. Results also indicate that the decrease in temperature at the Tg onset of Run 2 is proportional to the increased amount of Bioglass® ceramic in the wafers. The only exception to this trend was the treatment group B1.

High Performance Liquid Chromatography: To determine the molecular weight of the polymer wafers, high performance liquid chromatography (HPLC) was run using tetrahydrofuran (THF) as the solvent, with a 0.80 ml/min flowrate. Fifty µl were injected into a TosoH TSK-GEL 4000+3000 column at a concentration of 10.820 mg/ml with a column and detector temperature of 25° C. The increased addition of Bioglass® ceramic in the wafers resulted in a 10–15% decrease in Mw for all the groups. These results indicate an increased amount of Bioglass® ceramic added to the wafer is proportional to the decrease in Mw.

Gas Chromatography: To determine the residual acetone and ethanol levels, gas chromatography was performed using Hewlett Packard 6890 and running a FID protocol with nitrogen as the carrier gas. In all of Group C and Group A1 acetone levels above 100 ppm were detected at the time of testing. All other groups had either undetectable or a level below 100 ppm for residual acetone. Residual ethanol above 100 ppm was detected for Control Group C and Group C3. All other groups had undetectable amounts of residual ethanol.

With increased amount of Bioglass® ceramic added to the wafer, there is an increase in storage modulus of the DMA bars and a decrease in the Mw of the polymer. The 55/45 polymer groups showed the largest increase in storage modulus and the lowest drop in Run 2 Tg onset from control values. The DMA data showed no significant differences in bars tested from the end and center regions of the wafers. The Bioglass® ceramic with the larger particle size used in this experiment also results in a larger increase in storage modulus as compared to the Bioglass® ceramic with smaller particle sizes.

Example 6

Mechanical Properties of Fully-Dense Bioglass® Ceramic/Polymer Composites

Figure 5:
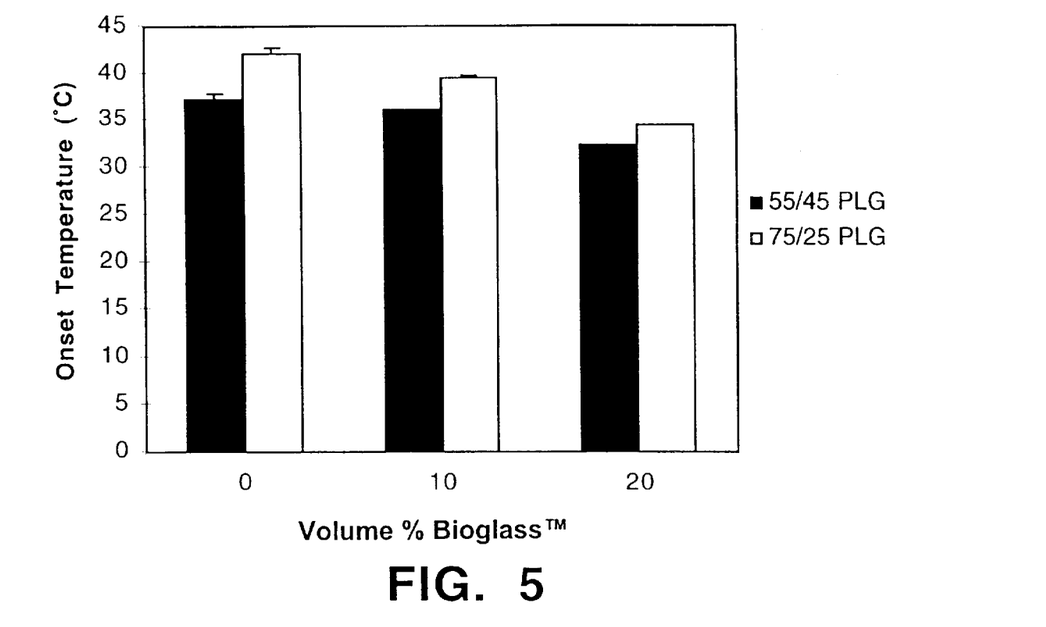
FIG. 5 shows variations of glass transition temperature as a result of Bioglass® ceramic content in fully dense polymer compositions comprising 55/45 and 75/25 PLG and 0, 10 and 20 volume percent Bioglass® tested wet.
Figure 6:
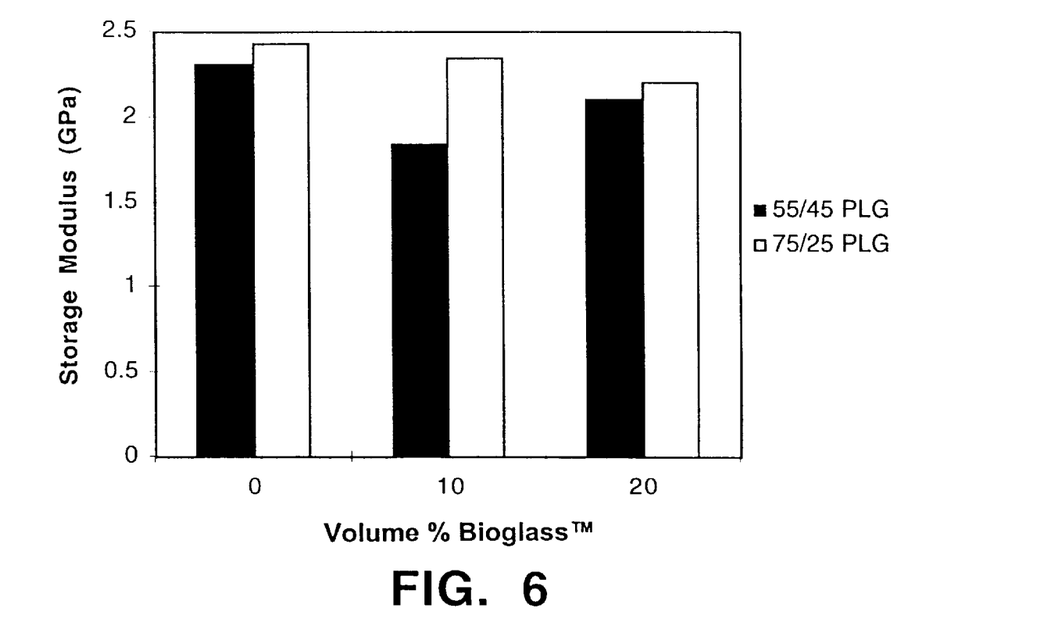
FIG. 6 shows variation of mechanical properties (storage modulus) at 37° C., wet, of fully-dense Bioglass®/polymer compositions comprising 55/45 and 75/25 PLG and 0, 10 and 20 volume percent non-surface-passivated Bioglass® ceramic.

The composite materials prepared in Example 2 were tested using the three-point bending test described in Example 5, except that the materials were tested at physiological conditions, i.e., 37° C. wet. The temperature was ranged from 15–50° C., at 1 Hz and 0.05% strain, and mean bending onset temperature (glass transition temperature) noted. Results are shown in FIGS. 5 and 6.

Molecular weights of the materials were as set forth in Table 2.

TABLE 2

| Sample | Molecular Weight ($M_W$) |
| --- | --- |
| 55/45 | 68,900 |
| 55/45, 10% Bioglass ® ceramic | 67,400 |
| 55/45, 20% Bioglass ® ceramic | 67,800 |
| 75/25 | 81,900 |
| 75/25, 10% Bioglass ® ceramic | 84,300 |
| 75/25, 20% Bioglass ® ceramic | 86,400 |

Figure 7:
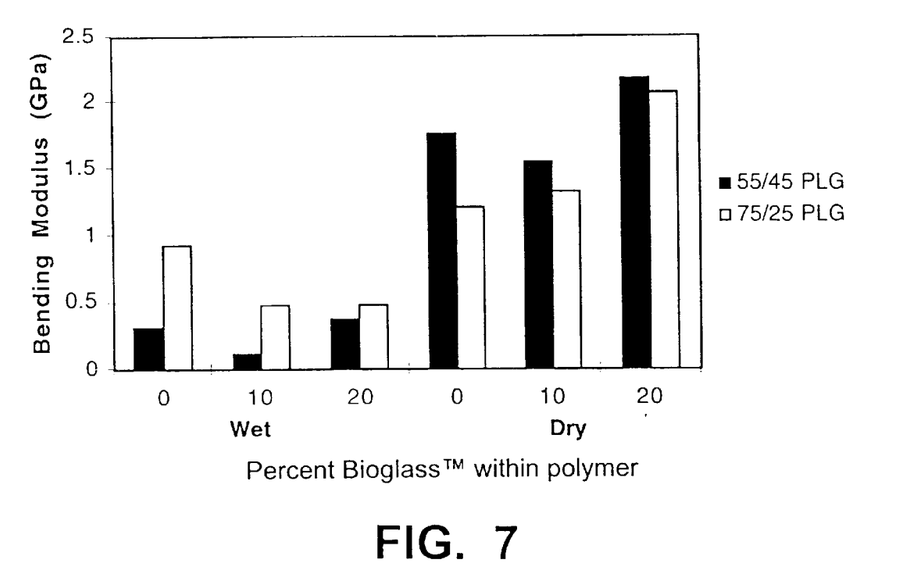
FIG. 7 compares the testing of mechanical properties (Young's modulus) at 37° C. under physiological (wet) conditions with the same tests made on dry materials containing non-surface-passivated Bioglass® ceramic. The darker bars represent wet test results and the lighter bars represent dry test results.
Figure 8:
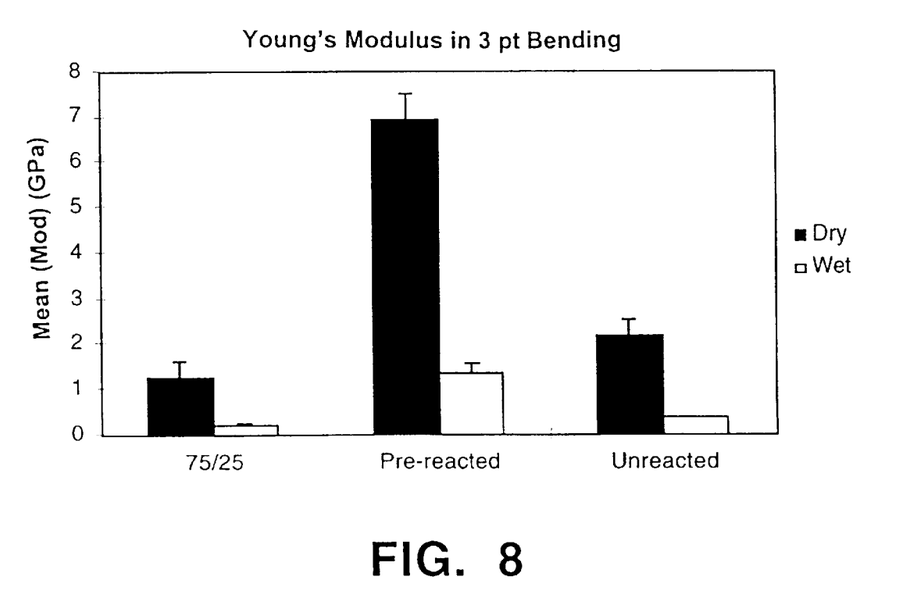
FIG. 8 compares tests of mechanical properties (Young's modulus) at 37° C. under physiological (wet) conditions using 75/25 PLG, 75/25 PLG containing 40 volume percent Bioglass® ceramic which has been surface-passivated by pre-reacting with water, and the same composite which has not been surface-passivated.
Figure 9:
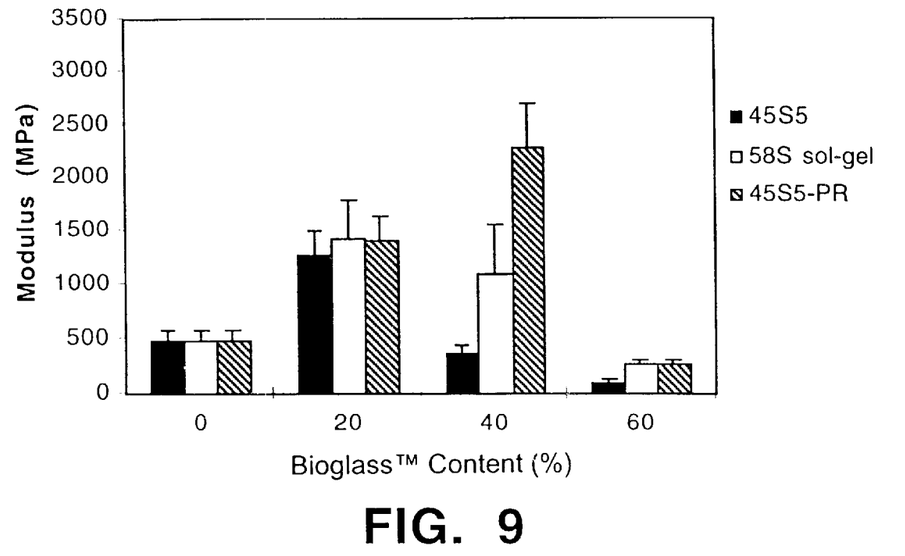
FIGS. 9 and 10 compare moduli of inventive (4555-PR) and prior art Bioglass® ceramic at various concentrations of the glass in lower molecular weight (MW) polymer (FIG. 9) and higher MW polymer (FIG. 10) composites.
Figure 10:
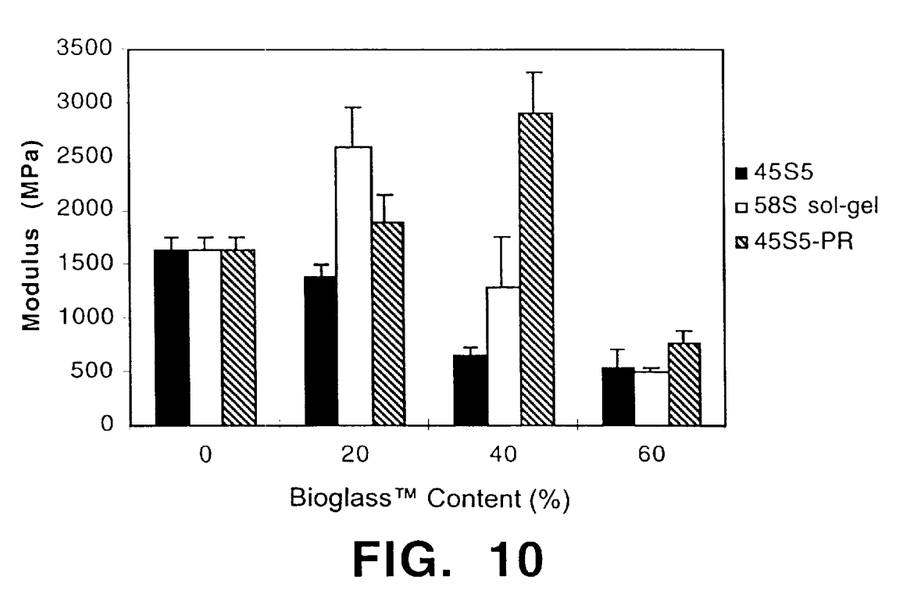

The bending tests were then performed on these materials in the dry state at 37° C. Results are shown in FIG. 7. These results shown that the storage modulus drops dramatically when tested under wet conditions. The modulus of the 55/45 material decreases or stays the same with 10 volume percent and 20 volume percent Bioglass® ceramic, whereas the modulus of the 75/25 materials decreases with the addition of Bioglass® ceramic. When tested dry, the storage modulus of these fully-dense materials behaves as expected, increasing with Bioglass® ceramic content. This decrease in storage modulus in wet material is believed due to the Bioglass® ceramic surface reaction with water, causing a failure of the interface between the Bioglass® ceramic particles and the polymer and resulting in an overall reduction in stiffness.

Example 7

Methods of Increasing Mechanical Properties of Bioglass® Ceramic/Polymer Composites.

A. Composite materials are made according to the procedures of Examples 1 and 2, except that prior to addition of Bioglass® ceramic to the polymer, the Bioglass® ceramic particles are soaked in a physiologically buffered solution to form a pre-reacted, passivated surface.

The materials are tested as described in Example 5 except that the materials are wet when tested. Comparable results showing increased mechanical properties in Bioglass® ceramic-containing composites are achieved.

B. Composite materials are made according to the procedures of Examples 1 and 2, except that a silane coupling agent is added to the polymer with the Bioglass® ceramic. The materials are tested as described in Example 5 except that the materials are wet when tested. Comparable results showing increased mechanical properties in Bioglass® ceramic-containing composites are achieved.

C. Composite materials are made according to the procedures of Examples 1 and 2 except that prior to addition of the Bioglass® ceramic to the polymer, it is pre-treated with polymer. A small quantity of polymer is dissolved in the solvent and Bioglass® ceramic is dispersed in the solution. The Bioglass® ceramic is then allowed to air dry or is dried in a fluidized bed or spray drying apparatus, followed by comminution to break up aggregates. The Bioglass® ceramic particles which are now coated with polymer are then mixed with additional polymer to form the composite.

The materials are tested as described in Example 5 except that the materials are wet when tested. Comparable results showing increased mechanical properties in Bioglass® ceramic-containing composites are achieved.

Example 8 pH of Bioglass® Ceramic/Polymer Composites.

Wafers of size 20×40×3 mm were made using the procedures of Example 1 using 75/25 D,L-PLG alone or with 20 volume percent Bioglass® ceramic, calcium carbonate or sodium bicarbonate. Residual solvents were completely removed by placing in a vacuum oven at 60–65° C. for at least 72 hours. Wafers were cut into approximately 10×10×3 mm samples and placed in approximately 40 ml phosphate buffered saline (PBS) with 0.01% thimerosal. Samples in the control group containing no additives showed an increase in pH from 7.33 to 7.38 over a 37-day period. Samples in the group containing Bioglass® ceramic showed an increase from 8.24 to 8.86 over the same period. Samples in the group containing calcium carbonate showed an increase from 8.50 to 8.8 over a 34-day period. Samples in the group containing sodium carbonate showed an increase from 7.39 to 8.61 over a 37-day period. Control samples and those containing sodium bicarbonate decreased slightly in size over the test period, while samples containing Bioglass® ceramic and calcium carbonate increased slightly in size over the test period.

Example 9

Surface Reactivity of Bioglass® Ceramic/Polymer Composition

Figure 4:
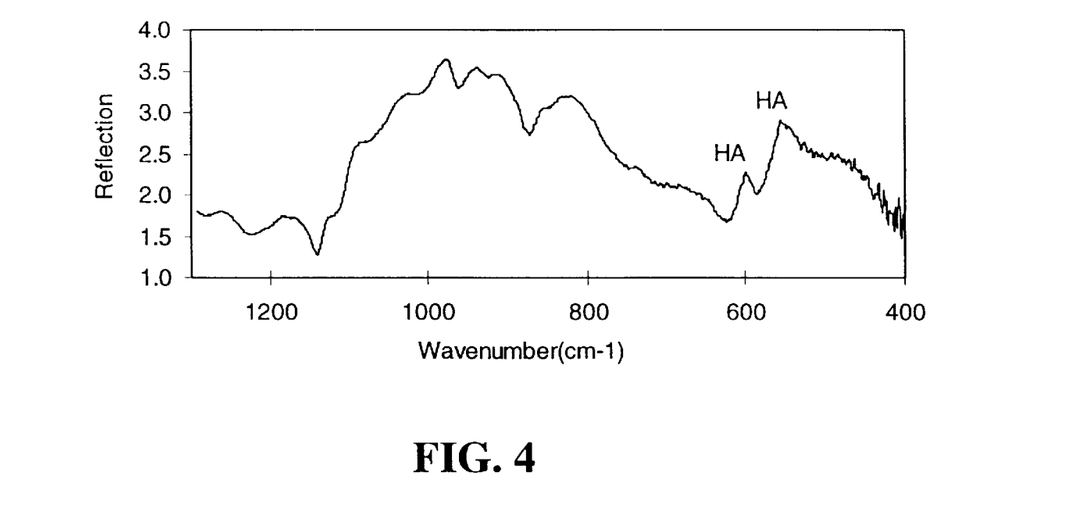
FIG. 4 shows Fourier transform infrared spectroscopy (FTIR) results on a porous Bioglass® ceramic/polymer composition containing 55/45 PLG and 20 volume percent Bioglass® after suspension in simulated body fluid (SBF) for six weeks, indicating formation of an apatite layer.

To characterize the surface-reactive properties of the composites, specimens of 55/45 D,L-PLG containing 5, 10 and 20 volume percent Bioglass® ceramic as described in Example 1 were suspended in simulated body fluid (SBF) for up to eight weeks at a surface area to volume ratio of 0.1 cm$^{-1}$ at 37° C. At the end of various reaction times, samples were removed and surface reactivity determined by Fourier Transform Infrared Spectroscopy (FTIR). At eight weeks, only composites with 20 volume percent Bioglass® ceramic showed formation of an apatite layer which promotes close interaction with bone. Results are shown in FIG. 4. Surface reactive properties can be tailored to the desired tissue by varying the Bioglass® ceramic type and concentration.

Example 10

Composite material of Example 2 was made containing 40 volume percent Bioglass® ceramic which had been surface-passivated by pre-reacting with water by adding 6.0 grams of Bioglass® ceramic to 1.0 liter of phosphate buffered saline, pH 7.4, and stirring gently for 24 hours at 37° C. The solution was filtered to recover the material, which was rinsed with deionized water and finally with acetone. The recovered Bioglass® ceramic was then dried under vacuum at 65° C. for two days. Recovery was about 75%. The surface-passivated Bioglass® ceramic/polymer composite was tested for mechanical properties (Young's modulus) at 37° C. wet against controls containing no Bioglass® ceramic and the same composite made using non-surface-passivated Bioglass® ceramic. The results are shown in Table 3.

TABLE 3

| Group | Dry Modulus (GPa) | Wet Modulus (GPa) |
|---|---|---|
| Pure polymer (75/25) | 1.288 ± 0.323 | 0.198 ± 0.038 |
| Unreacted Bioglass ® ceramic | 2.226 ± 0.317 | 0.360 ± 0.015 |
| Pre-reacted Bioglass ® ceramic | 6.957 ± 0.546 | 1.367 ± 0.206 |

These tests show that a composite material having mechanical properties similar to those of cortical bone under physiological conditions (wet, 37° C.) containing bioactive ceramic can be made by pre-reacting the bioactive ceramic to form an apatitic, surface-passivated layer.

We claim:

1. A therapeutic implant material comprising a surface-passivated bioactive ceramic mixed with a biodegradable synthetic polymer in an amount sufficient to produce enhanced mechanical properties in said implant material.

2. An implant material of claim 1 wherein said bioactive ceramic is present in an amount less than about 70 percent, based on the volume of the material.

3. A porous implant material of claim 1 having a selected Young's Modulus under physiological conditions of between about 0.1 MPa and about 100 MPa.

4. An implant material of claim 1 wherein the bioactive ceramic has been surface-passivated by pre-reacting with an aqueous solution.

5. An implant material of claim 1 also comprising a silane coupling agent.

6. An implant material of claim 1 wherein said polymer in the finished implant material has a selected weight average molecular weight between about 25,000 and about 1,000,000.

7. An implant material of claim 1 comprising a first section comprising bioactive ceramic adapted for bonding to soft connective tissue and a second section comprising bioactive ceramic adapted for bonding to hard connective tissue.

8. A method of using an implant material of claim 1 comprising forming said material into an implant device selected from the group consisting of: tissue scaffolds, granular bone graft substitute material, two-phase osteochondral implants, weight bearing bone implants, tacks, pins, screws, bone onlays, and films.

9. An implant material of claim 1 wherein said material is biodegradable.

10. An implant material of claim 1 also comprising surface-active bioactive ceramic.

11. An implant material of claim 1 wherein said biodegradable polymer is selected from the group consisting of polylactic acid (PLA) polymers, polyglycolic acid (PGA) polymers, and copolymers of PLA and PGA.

12. An implant material of claim 1 wherein said biodegradable polymer is a copolymer of PLA and PGA comprising between about 15 and about 50 percent PGA.

13. An implant material of claim 1 which has a selected target porosity greater than about 50 percent, based on the volume of the material.

14. An implant material of claim 1 which has a selected target porosity less than about 75 percent, based on the volume of the material.

15. A therapeutic implant material comprising a surface-passivated bioactive ceramic mixed with a biodegradable polymer in an amount sufficient to produce enhanced mechanical properties in said implant material, said material having a selected target porosity.

16. An implant material of claim 15 wherein said selected target porosity is greater than about 50 percent of the volume of said material, based on the volume of the material.

17. A method of making a porous implant material of claim 15 comprising:
    (a) mixing said polymer with a polymer solvent;
    (b) mixing said bioactive ceramic with said dissolved polymer;
    (c) placing said mixture of step (b) into a mold and incubating under vacuum pressure conditions to produce said porous implant material.

18. A method of making a substantially nonporous implant material comprising a surface-passivated bioactive ceramic mixed with a biodegradable polymer in an amount sufficient to produce enhanced mechanical properties in said implant material, said method comprising:
    (a) mixing said polymer with a polymer solvent;
    (b) mixing said bioactive ceramic with said dissolved polymer;
    (c) incubating said mixture of step (b) under pressure to produce said implant material.

19. A therapeutic implant material comprising a surface-passivated bioactive glass mixed with a biodegradable polymer in an amount sufficient to produce enhanced mechanical properties in said implant material.

20. An implant material of claim 19 having a selected Young's Modulus under physiological conditions of between about 0.1 MPa and about 100 MPa.

21. An implant material of claim 19 also comprising a surface-active bioactive ceramic.

22. An implant material of claim 19 also comprising a silane coupling agent.

23. An implant material of claim 19 wherein said polymer in the finished implant material has a selected weight average molecular weight between about 25,000 and about 1,000,000.

24. A method of using an implant material of claim 19 comprising forming said material into an implant device selected from the group consisting of: tissue scaffolds, granular bone graft substitute material, two-phase osteochondral implants, weight bearing bone implants, tacks, pins, screws, bone onlays, and films.

25. An implant material of claim 19 wherein said material is wholly biodegradable.

26. An implant material of claim 19 wherein said bioactive glass comprises $SiO_2$, $CaO$, and $Na_2O$.

27. A biodegradable film for application to a wound comprising a biodegradable polymer and between about 10 and about 70 percent of a surface-passivated bioactive ceramic.

* * * * *

UNITED STATES PATENT AND TRADEMARK OFFICE
CERTIFICATE OF CORRECTION

PATENT NO. : 5,977,204

DATED : November 2, 1999

INVENTOR(S) : Boyan et al.

It is certified that error appears in the above-identified patent and that said Letters Patent is hereby corrected as shown below:

Title page, inventors;
Please delete the first named inventor "Barbara D. Boyan" in item [75] of the first page of the patent. The correct order of inventors is: --Gabriele Niederauer, Kristine Kieswetter, Neil C. Leatherbury and David C. Greenspan--.

Signed and Sealed this

Sixth Day of June, 2000

Attest:

Q. TODD DICKINSON

*Attesting Officer*

*Director of Patents and Trademarks*